United States Patent [19]
Orth et al.

[11] Patent Number: 5,681,346
[45] Date of Patent: Oct. 28, 1997

[54] EXPANDABLE STENT FORMING PROJECTING BARBS AND METHOD FOR DEPLOYING

[75] Inventors: Geoffrey A. Orth, La Granada; Scott C. Anderson, Sunnyvale; Peter S. Brown, Mountain View, all of Calif.

[73] Assignee: Advanced Cardiovascular Systems, Inc., Santa Clara, Calif.

[21] Appl. No.: 779,086

[22] Filed: Jan. 6, 1997

Related U.S. Application Data

[62] Division of Ser. No. 405,265, Mar. 14, 1995, Pat. No. 5,591,197.

[51] Int. Cl.$^6$ .................................................. A61F 2/04
[52] U.S. Cl. .............................. 606/198; 606/194; 623/1
[58] Field of Search ........................... 606/198, 191, 606/192, 194, 195; 623/1, 12

[56] References Cited

U.S. PATENT DOCUMENTS

| | | | |
|---|---|---|---|
| 3,657,744 | 4/1972 | Ersek | 623/11 |
| 4,650,466 | 3/1987 | Luther . | |
| 4,733,665 | 3/1988 | Palmaz | 606/108 |
| 4,739,762 | 4/1988 | Palmaz | 623/1 |
| 4,893,623 | 1/1990 | Rosenbluth | 606/192 |
| 5,007,926 | 4/1991 | Derbyshire | 623/1 |
| 5,034,001 | 7/1991 | Garrison et al. | 604/53 |
| 5,219,355 | 6/1993 | Parodi et al. . | |
| 5,236,446 | 8/1993 | Dumon | 623/1 |
| 5,397,355 | 3/1995 | Marin et al. | 623/12 |
| 5,443,496 | 8/1995 | Schwartz | 623/1 |
| 5,449,373 | 9/1995 | Pinchasik et al. | 606/198 |
| 5,591,197 | 1/1997 | Orth et al. | 606/198 |

FOREIGN PATENT DOCUMENTS

| | | |
|---|---|---|
| 0 335 341 A1 | 10/1989 | European Pat. Off. . |
| 0 462 008 A1 | 12/1991 | European Pat. Off. . |
| 0 540 290 A2 | 5/1993 | European Pat. Off. . |
| 0 579 523 A1 | 1/1994 | European Pat. Off. . |
| 0 621 016 A1 | 10/1994 | European Pat. Off. . |
| 43 03 181 | 8/1994 | Germany . |
| 1205743 | 9/1970 | WIPO . |
| WO 92/06734 | 4/1992 | WIPO . |

*Primary Examiner*—Michael Buiz
*Assistant Examiner*—Patrick W. Rasche
*Attorney, Agent, or Firm*—Fulwider Patton Lee & Utecht

[57] ABSTRACT

An intraluminal stent for implanting in a body lumen in which a plurality of connecting members are deformed radially outwardly to form projecting barbs for attaching the stent to a body lumen. The stent has a first, unexpanded low profile diameter for intraluminal delivery, and a second, larger expanded diameter for implanting in a body lumen in which projecting barbs are formed and which penetrate the body lumen to assist in attaching the stent to the walls of the body lumen.

5 Claims, 9 Drawing Sheets

EXPANDABLE STENT FORMING PROJECTING BARBS AND METHOD FOR DEPLOYING

This is a division, of application Ser. No. 08/405,265, filed Mar. 14, 1995 now U.S. Pat. No. 5,591,197.

The invention relates generally to endoprostheses and, more specifically, to an intraluminal stent for repairing a damaged or diseased artery, or to be used in conjunction with a tube graft for delivery to an area of a body lumen that has been weakened by damage or disease, such as an aneurysm of the abdominal aorta. Several areas of the body are particularly suitable for receiving an endoprosthesis, commonly referred to as an intraluminal stent to hold open and insure the patency of a body lumen. Two such areas include the coronary arteries and the aorta, especially in the area where an aneurysm has developed.

An abdominal aortic aneurysm ("AAA") is an abnormal dilation of the arterial wall of the aorta in the region of the aorta that passes through the abdominal cavity. The condition most commonly results from atherosclerotic disease. Frequently, abdominal aortic aneurysms are dissecting aneurysms, that is aneurysms that are formed when there is a tear or fissure in the arterial lining or wall through which blood is forced and eventually clots, forming a thrombosis which swells and weakens the vessel. Abdominal aortic aneurysms do not cause pain, but are easily detected in a thorough physical examination. If the aneurysm is not detected and treated, it is likely to rupture and cause massive hemorrhaging fatal to the patient.

Treatment of AAAs comprises some form of arterial reconstructive surgery which commonly is referred to as a "triple-A" procedure. One such method is by-pass surgery, in which an incision is made into the abdominal cavity, the aorta is closed off above and below the site of the aneurysm, the aneurysm is resected, and a synthetic graft or tube sized to approximate the diameter of the normal aorta is sutured to the vessel to replace the aneurysm and to allow blood flow through the aorta to be reestablished. The graft commonly is fabricated of a biocompatible material that is compliant and thin-walled. Nylons and synthetic fibers such as those manufactured under the trademarks DACRON or TEFLON have been found to be suitable for the construction of the graft. Studies have shown that the mortality rate associated with this surgical procedure is favorable (less than 5%). when it is performed prior to rupture of an aneurysm. However, patients having an AAA typically are over 65 years of age, and often have other chronic illnesses which increase the risk of perioperative or post-operative complications. Those patients thus are not ideal candidates for this type of major surgery. Further, it has been pointed out that this procedure is not often successfully resorted to after an aneurysm has ruptured (the mortality rate increases to over 65%) because of the extensiveness of the surgery and the time required to prepare a patient for it.

Because of the aforementioned disadvantages to conventional surgical methods, another procedure was developed as an alternative to conventional, major surgery. This method also involves emplacement of a graft at the site of the aneurysm; however, the graft is deployed there by being routed through the vascular system carried by a catheter, wire or other device suitable for negotiating the vasculature. The graft and its deployment system often are introduced into the blood stream percutaneously with a femoral approach and the entire procedure can be performed using local rather than general anesthesia.

Once the graft has been positioned at the aneurysm, it is disengaged from the delivery system and can be affixed to the aortic wall both distally and proximally of the aneurysm. For this purpose, grafting systems usually include fixation means such as staples or hooks which can be manipulated and driven into the intima of the vessel via some mechanical feature of the system, or by some physical process, such as expansion of the graft through application of pressure. To avoid premature detachment of the graft and to prevent the attachment elements from damaging the vessels or halting the forward movement of the system while the graft is being routed to the treatment site, the systems often are provided with a feature such as a capsule or a sheath that protects and contains the graft until such time as deployment is desired.

Once the graft is in place, it is positioned in the vessel spanning the site of the aneurysm such that the walls of the graft are generally parallel to the walls of the affected area of the aorta. The aneurysm thus is excluded from the circulatory system by the graft rather than being resected altogether. If the aneurysm is a dissecting type and a thrombosis exists between the walls of the aorta, the now-excluded aneurysm may beneficially provide structural support for the graft.

Grafting systems are known that include what commonly is referred to as an attachment system for deploying the graft. The attachment system is a tubular device which is fitted inside and is generally coaxial with the graft, and which can extend out of the graft at either or both the proximal and distal ends thereof. The attachment system often has a lattice-like or open weave structure, which provides it with flexibility and which promotes rapid endothelial tissue growth through the structure once the graft has been deployed. It may be provided with additional hook-like elements for penetration of the intimal walls for attachment of the graft to the aorta, or those hook-like elements may be provided on the graft itself. Graft systems of type described can be found in U.S. Pat. Nos. 4,787,899 (Lazarus); 5,104,399 (Lazarus); 5,219,355 (Parodi et al.); and 5,275,622 (Lazarus), which are incorporated herein by reference. A stent and graft combination can be found in U.S. Ser. No. 340,112, filed Nov. 15, 1994, which is commonly assigned to the same assignee as the present invention, namely Advanced Cardiovascular Systems, Inc., Santa Clara, Calif. U.S. Ser. No. 340,112 also is incorporated herein by reference. Generally, prior art systems that employ attachment means which include hooks or staples create a very large profile for delivery through a body lumen.

The actual function of delivering the graft may be accomplished by inflating a balloon of a catheter by introducing pressurized fluid into a lumen of the catheter from a source external to the patient. Inflation of the balloon applies a force to the graft and any attachment system supplied therein which extends radially and presses the graft and attachment system into the vessel wall just above and just below the aneurysm. Other devices used to attach a graft to the aortic wall for AAA repair include intravascular stents of the type found in U.S. Pat. No. 5,316,023.

In order for a stent to be used most advantageously with a graft deployment system for treatment and repair of aneurysms, the stent must be composed of a biocompatible material and must be simultaneously flexible enough to comply with the catheter or other element used to route the graft through the often tortuous vascular path to the site of the aneurysm and strong enough radially to maintain the opening in the graft once delivered. It is important that the stent or stent-and-graft combination have a low profile for intraluminal delivery. The stent must be well suited to deployment by a delivery system that is not overly complex, and thus is reliable and easy to operate. Further, it is desirable that the stent be expandable, so that upon application of a force or physical change from within sufficient to cause radial expansion, it encourages affixation of itself and the graft to the aortic walls. Although various stents have been proposed, none adequately provides all of these desirable features.

Another area in which stents have commonly been used are in the coronary arteries for the purpose of repairing a damaged or diseased vessel. In typical prior art situations, the stent is mounted on the balloon portion of a catheter and is delivered intraluminally by known methods to a specific location in a coronary artery. Generally, a stent is deployed after a patient has undergone a PTCA (percutaneous transluminal coronary angioplasty) procedure in which a lesion or other obstruction in the artery has been dilated by known methods. Deploying an intravascular stent at the site where an angioplasty has occurred will reduce the likelihood of a restenosis and can assist in tacking up any dissections and in general reinforce the vessel wall.

Most, but not all, stents currently described in the art provide a smooth outer wall surface which, when expanded, do not penetrate into the vessel wall. Thus, some prior art stents do not provide adequate fixation methods to attach the stent to the vessel wall during deployment.

What has been needed and heretofore unavailable is a stent for use in combination with a graft which has a high degree of flexibility for efficient advancement through tortuous passageways, which can be radially expanded from a relatively small diameter and low profile to a relatively large diameter without substantial longitudinal contraction, and which exhibits mechanical strength sufficient to penetrate the vessel walls thereby resisting migration and to maintain the patency of a synthetic graft implanted at the site of an aneurysm. The present invention satisfies this need.

SUMMARY OF THE INVENTION

The present invention is directed to an intravascular stent which can be used in combination with an aortic graft to repair an abdominal aneurysm or it can be used separately to reinforce a coronary artery after a PTCA procedure. As used herein, reference to the "proximal" is toward the outside of the patient and away from the stent while reference to the "distal" is toward the stent which is generally mounted on the balloon portion of a catheter. The proximal and distal definitions apply equally to directions in the vascular system and especially in the aorta and the coronary arteries.

In a preferred embodiment, the stent of the present invention is attached to the distal end of a tubular graft such that at least a portion of the stent is exposed distally beyond the distal end of the graft. Thereafter, the graft-and-stent combination are deployed intraluminally such that the stent and the distal end of the graft are positioned distally of the aneurysm while the proximal end of the graft extends proximally of the aneurysm. Thus, the tubular graft will span the diseased area of the aneurysm.

The intravascular stent is comprised of a plurality of cylindrical elements that are interconnected to each other by a plurality of connecting members. The cylindrical elements on a first stent section face one direction and in a second stent section the cylindrical elements face the opposite direction. At least some of the connecting members between the first and second stent sections have a notch to create a weakened area which will permit the connecting member to deform or buckle outwardly when the stent is expanded. More than one notch can be formed in the connecting members. When the stent is expanded from a low profile, first diameter, the connecting members having a notch will buckle outwardly forming a projecting barb which will penetrate the aortic wall and thereby attach the stent-and-graft combination to the aortic wall. Because the first and second stent sections have oppositely facing cylindrical elements, during expansion a compression force is created which causes the connecting members to buckle at the notched area. Several of these projecting barbs may be employed to affix the stent-and-graft combination. It is also possible to attach a stent to the proximal end of the tubular graft to affix the proximal portion of the tubular graft to the aortic wall. Further, it is envisioned that the stent can be employed with a bifurcated graft (not shown) which is generally used when the aortic aneurysm is close to the aortic bifurcation.

In another embodiment of the invention, the connector members having a notch are offset or angulated from the longitudinal axis of the stent. When the stent is rotated or twisted the connecting members are compressed forcing them to align and buckle outwardly to provide projecting barbs as described above. Rotating the stent can be accomplished in numerous ways, including holding one end stationary while rotating the other end, or counter-rotating each of the ends respective to each other. This rotational or twisting action will cause the connecting members having a notch to buckle outwardly as long as the overall length of the stent does not appreciably increase. This embodiment can be used as described above with a stent and graft combination for repairing aortic aneurysms.

A further embodiment of the invention includes an intravascular stent having a first stent section and a second stent section, each section having a plurality of oppositely facing cylindrical elements connected by a plurality of connecting members. Some of the connecting members have one or more notches which provide a weakened area in the connector member. When the ends of the stent are moved toward each other, this causes the weakened area or notch in the connecting members to deform so that the connecting member buckles outwardly to form a projecting barb. This embodiment of the stent also can be used with a stent-and-graft combination to repair an aortic aneurysm.

It also is contemplated that each of the embodiments can be used to repair other body lumens such as the coronary arteries. Thus, for example, the stent of the present invention can be implanted in a coronary artery after a PTCA procedure in order to repair a damaged or diseased portion of the artery. The stent will be deployed and implanted similar to that described above, with the exception that the projecting barbs will correspondingly be smaller in the coronary arteries than in the aorta. The projecting barbs will assist in firmly attaching the stent to the vessel wall so that it is more securely attached to the vessel wall once it has been implanted. A clear advantage of the stent for use in the coronary arteries is its low delivery profile and its positive attachment features upon implanting.

In another embodiment of the invention, the notched connecting member has a beveled-edge member affixed to at least a portion of the connecting member by any known means, such as by welding. The beveled-edge member has a point that extends outwardly from the outward-most portion of the projecting barb so that the beveled-edge member and the projecting barb penetrate the vessel wall.

Other features and advantages of the present invention will become more apparent from the following detailed description of the invention, and taken in conjunction with the accompanying exemplary drawings.

DETAILED DESCRIPTION OF THE PREFERRED EMBODIMENTS

The invention relates to an intravascular stent, one or more of which is used in conjunction with a known tubular graft or bifurcated graft for repairing body lumens of all types. As described herein, reference is made to repairing an aortic aneurysm, coronary arteries, and other vessels, however, other body lumens are equally suited to receive the stent of the present invention.

Figure 1:
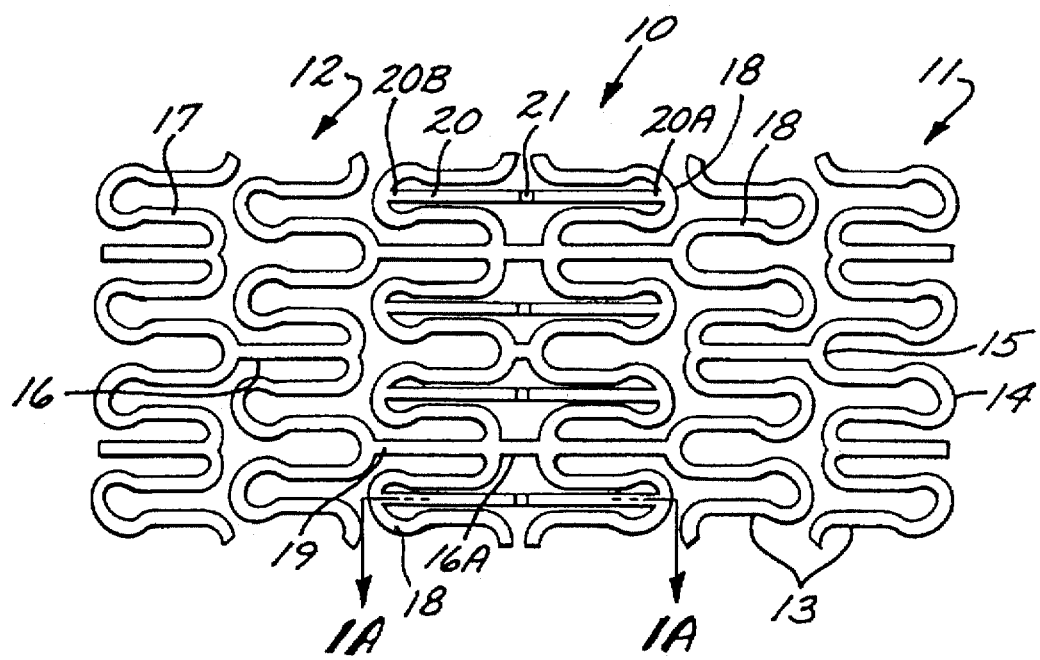
FIG. 1 is a plan view depicting the stent of the present invention having a plurality of connecting members which will become projecting barbs upon expansion.
Figure 1A:
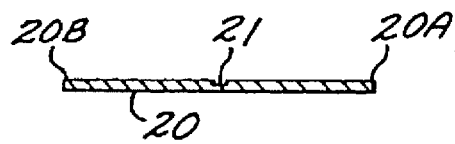
FIG. 1A is a cross-sectional view taken along lines 1A—1A depicting a connecting member having a weakened area or notch.
Figure 1B:
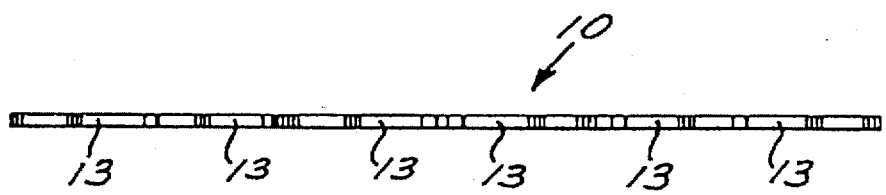
FIG. 1B is an elevational view of the stent of FIG. 1 where the notched connecting members have not been deformed.
Figure 2G:
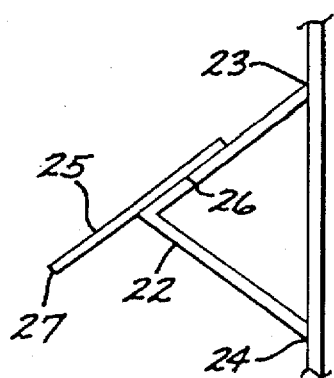
FIG. 2G is a side view of the connecting member of FIG. 2F depicting the connecting member buckled outwardly and forming a projecting barb and depicting the beveled-edge member projecting outwardly for deeper penetration into the vessel wall.
Figure 2:
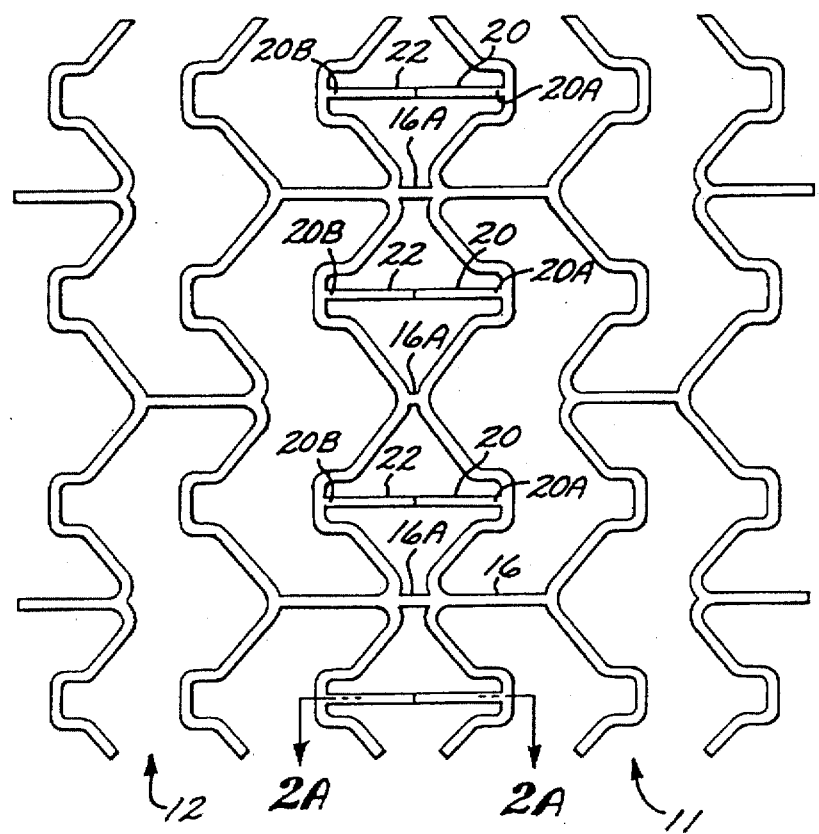
FIG. 2 is a plan view depicting the stent of FIG. 1 in which the stent has been expanded.
Figure 2A:
FIG. 2A is cross-sectional view taken along lines 2A—2A depicting the notched connecting member in its deformed configuration as a projecting barb.
Figure 2B:
FIG. 2B is an elevational view of the expanded stent of FIG. 1 depicting the notched connecting member projecting outwardly as a projecting barb.
Figure 2C:
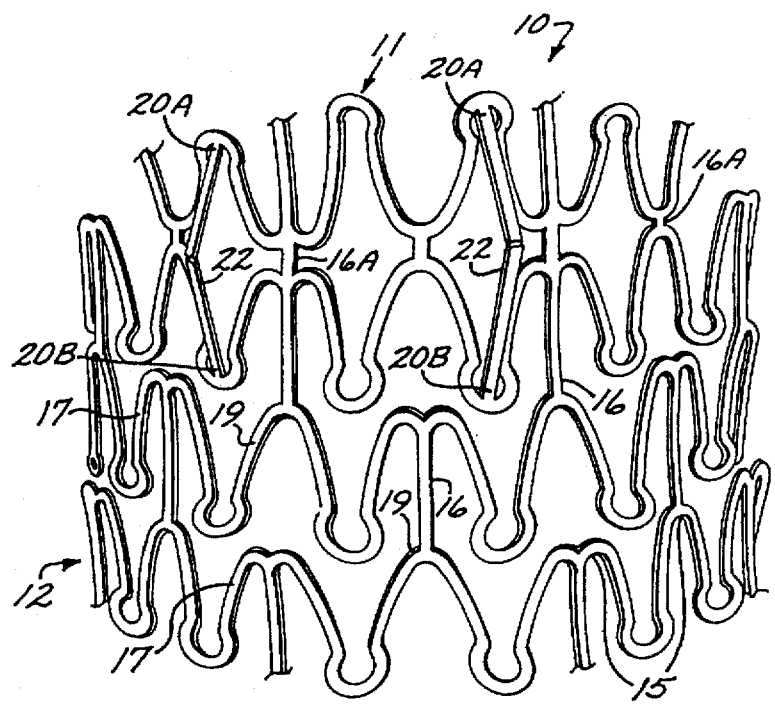
FIG. 2C is a partial elevational view of the stent of FIG. 2 rolled into a cylindrical configuration and depicting the projecting barbs as they appear projecting outwardly when the stent is expanded.
Figure 2D:
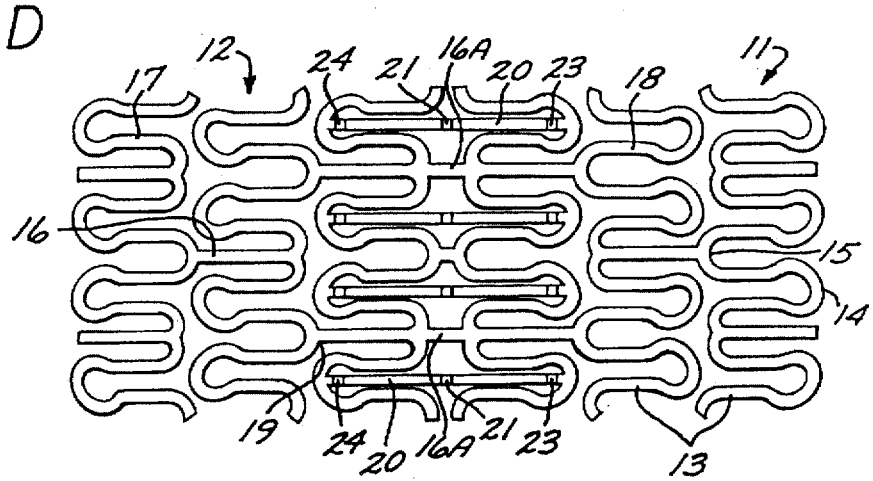
FIG. 2D is a plan view depicting the stent of FIG. 1 in which the notched connecting members each have more than one notched or weakened portion to facilitate deformation of the connecting member.

In keeping with the invention, FIGS. 1–2D depict an intravascular stent 10 having a first stent section 11 and a second stent section 12. In the embodiment shown, each of first stent section 11 and second stent section 12 have a plurality of cylindrical elements 13 which are connected by a plurality of connecting members 16. Each of cylindrical elements 13 are comprised of a series of peaks 14 and valleys 15 in a serpentine manner. As depicted in FIGS. 1–1B, stent 10 is in a flattened condition and can be formed from a flat sheet of material as will be described herein. Stent 10 also can be formed from a piece of tubing using known chemical etching or laser cutting techniques.

Due to the serpentine nature of cylindrical elements 13, in addition to the connecting members 16, there appears a pattern of W-members 17, U-members 18, and Y-members 19. As can be seen, the radii in the various W-, U-and Y-members are different to accommodate differing expansion rates of the various members and to provide more uniform expansion as will be described herein.

In a preferred embodiment, first section 11 and second section 12 are connected by a plurality of notched connecting members 20 which are designed to buckle or deform during expansion of stent 10. To accomplish the proper deformation of notched connecting member 20, a notch 21 is cut into notch connecting member 20 to provide a weakened area and to allow deformation to take place at that point. As can be seen in FIG. 1A, notch 21 is cut a distance into notched connecting member 20, but not all the way through. It is intended that notched connecting member 20 deform and buckle during expansion, but not to break apart at notch 20. Thus, notch 20 is to be cut into connecting member 20 a distance sufficient to cause a weakened area, but not so deep as to cause failure and breaking of notched connecting member 20 at the notched area. Notched connecting member 20 also can have several more notches so that connecting member 20 can buckle more easily. Thus, end notches 23,24 near the ends of connecting member 20 will enable the connecting member to buckle more easily and thereby form projecting barb 22.

Figure 1C:
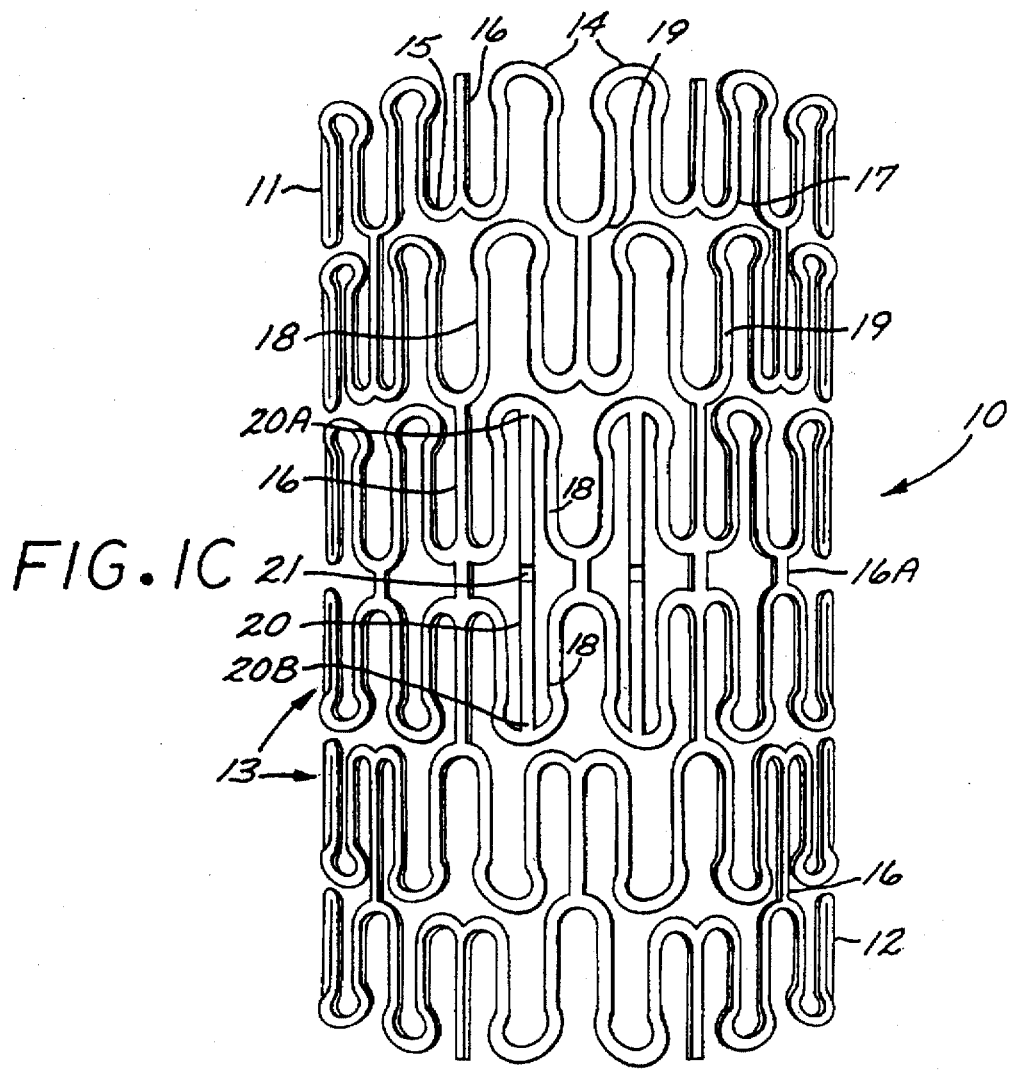
FIG. 1C is a perspective-elevational view of the stent of FIG. 1 rolled into a cylindrical configuration but not expanded (the backside of the cylinder is not shown for clarity purposes).

Turning to FIG. 1C, the flat sheet of stent 10 as depicted in FIG. 1 has been rolled into a cylindrical configuration with the back side of the stent not shown for clarity purposes. Also, only two notched connecting members 20 are depicted, however, any number of notched connecting members 20 can be provided to accomplish the intended use. Stent 10 of FIG. 1C is in a non-expanded configuration. When the stent 10 is manufactured from a flat sheet of material as depicted in FIG. 1, it must be rolled into the cylindrical configuration depicted in FIG. 1C and the longitudinal ends of the stent must be welded, brazed, soldered or joined together by any known means. The stent of FIG. 1C also can be formed from a single piece of tubing thus eliminating the steps of rolling it into a cylindrical configuration and affixing the longitudinal ends.

FIGS. 2–2B depict stent 10 as it is formed from a flat sheet of material and in its expanded configuration. These drawing figures provide a clear picture of the expansion properties of stent 10 and its impact on notched connecting member 20, but in use stent 10 would not be expanded in its flattened configuration. As shown in FIG. 2, when stent 10 is expanded, the W-, U- and Y-members are deformed, however, their distance from one another remains substantially the same because connecting members 16, which separate each of cylindrical elements 13, do not change in length. Importantly, the length of notched connecting member 20 changes in response to the bending and expansion of U-members when stent 10 is expanded outwardly. As expansion occurs, connecting members 16, which connect first stent section 11 to second stent section 12, are in tension but they cannot stretch. This tension creates an opposite compressive force on connecting member 20 which buckles at notch 22 and shortens in length, thereby forming projecting barb 22. When the expansion occurs, the weakened area of notch 21 allows notched connecting member 20 to deform thereby forming projecting barb 22 as depicted in FIGS. 2A and 2B. All of the connecting members 16 not having notches, do not deform and do not buckle, they remain the same length thereby providing an expanded stent that does not appreciably shorten during expansion.

The stent shown in FIG. 2C is the stent of FIG. 2 rolled into a cylindrical configuration and expanded. Only one cylindrical element of first stent section 11 is depicted and it is shown connected to second stent section 12. As can be clearly seen, notched connecting member 20 has deformed radially outwardly resulting in projecting barb 22. It is intended that projecting barbs 22 contact and penetrate the vessel wall to assist in affixing stent 10 during the deployment and implanting procedure as will be further described.

It is important to note that with the present invention, the unexpanded stent 10 of FIG. 1C has an extremely low profile which allows the stent to be deployed through the vascular system with relative ease. Only after the stent has been positioned at the site at which it will be implanted, is it expanded and projecting barbs 22 form during radial expansion. Thus, the present invention provides a clear advantage over prior art devices where the delivery profile is substantially higher because of attachment hooks or other attachment devices increasing the profile rather than projecting outwardly during expansion as with the present invention.

In FIG. 2D the stent of FIG. 1 is depicted only there is more than one notch 21 to facilitate deformation of connecting members 20 into projecting barbs 22. The notches 21 will provide weakened areas in connecting members 20. When the stent is expanded from its first, low profile diameter, the weakened areas around notches 21 allow connecting members 20 to buckle and deform outwardly to form projecting barbs 22.

Figure 2F:
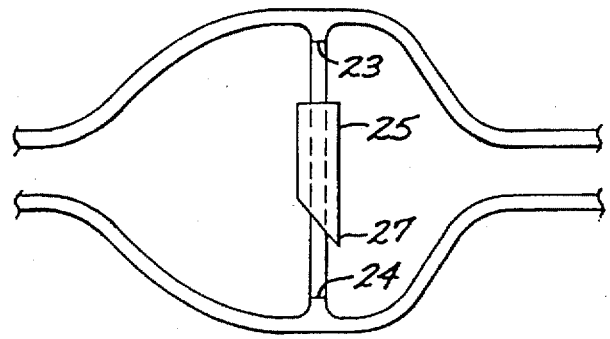
FIG. 2F is a plan view of the connecting member of FIG. 2E in which the stent has been expanded causing the connecting member to compress and to project outwardly so that the projecting barb and the beveled-edge member project outwardly.
Figure 2E:
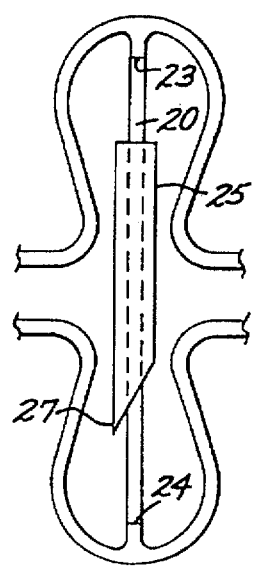
FIG. 2E is a partial plan view of one of the notched connecting members having a beveled-edge member affixed to a portion of the connecting member, the view being depicted in an unexpanded configuration.

In the event it is desirable to increase the depth projecting barbs 22 penetrate into the vessel wall, a beveled-edge member 25 can be attached to connecting members 20. As can be seen in FIGS. 2E–2G, beveled-edge member 25 is attached to connecting member 20 at point 26 by any known method, such as by welding, soldering or brazing. As described above, when the stent is expanded the distance from one end of the connecting member 20 to the other end become shorter causing connecting member 20 to buckle or deform outwardly thereby forming projecting barbs 22. As can be seen more clearly in FIG. 2G, when projecting barb 22 projects outwardly, beveled-edge member 25 projects even further outwardly providing a barb that will penetrate even deeper into a vessel wall.

One important feature of the present invention is that first stent section 11 and second stent section 12 are aligned so that the "U"-shaped members 18 oppose one another. The peaks of the U's are attached by short connecting members 16A, while the base of the U's are connected by the longer, notched connecting members 20 that have been weakened (by notches or by other means as described herein). When the stent is expanded from its low-profile first diameter to its expanded second diameter, short connecting members 16A are placed in tension against the longer connecting members 20 which are in compression. In order for the cylindrical elements 13 connected by long connecting members 20 and short connecting members 16A to expand, one of the two connecting members must fail. Because the compression-loaded longer connecting members 20 are inherently weaker than the tension-loaded short connecting members 16A, the longer connecting members 20 will fail. Since the long connecting members 20 are selectively weakened, such as by notch 21, they will selectively, and by design, fail outwardly to create projecting barbs 22.

Figure 3:
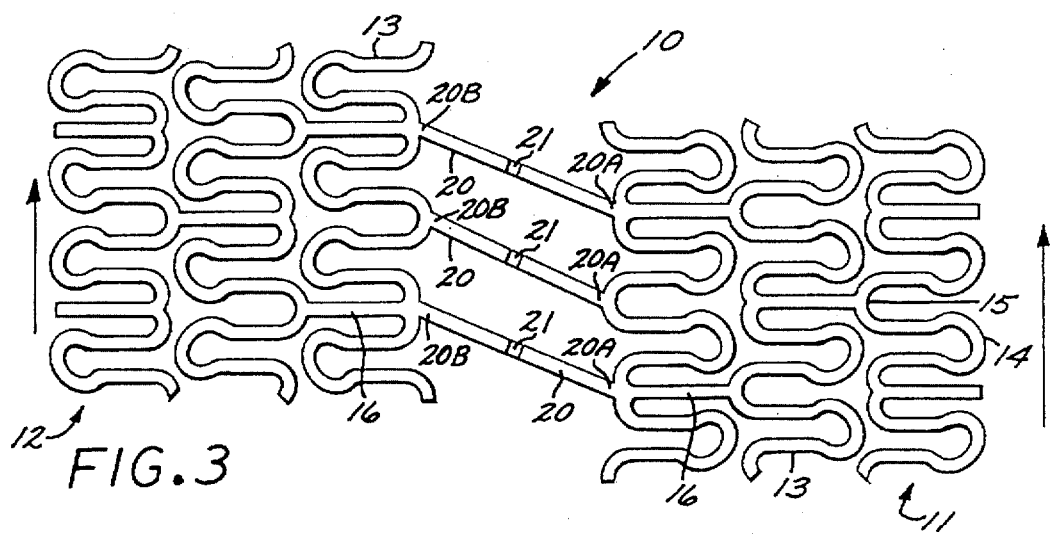
FIG. 3 is a plan view depicting another embodiment of the stent having connector members angulated or offset from the longitudinal axis of the stent.
Figure 3A:
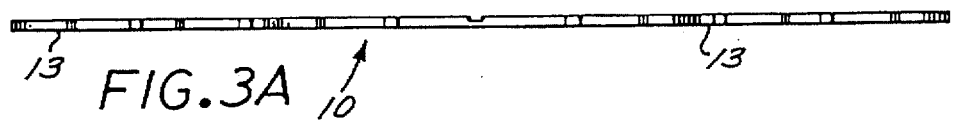
FIG. 3A is an elevational view of the stent of FIG. 3 depicting the stent in its flat and unexpanded configuration.
Figure 4:
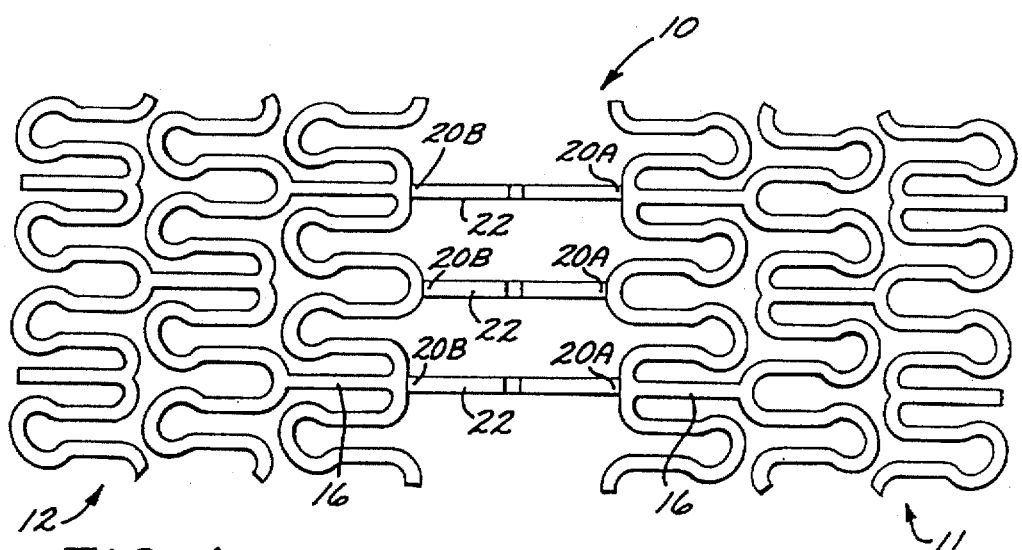
FIG. 4 is a plan view of the stent of FIG. 3 in an unexpanded configuration but with the two stent sections aligned such that the connector members having a notch have been twisted to project outwardly as projecting barbs.
Figure 4A:
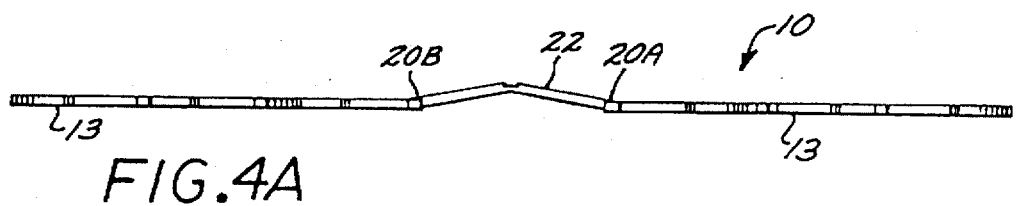
FIG. 4A is a plan view of the stent of FIG. 4 in which the connector members having a notch are projecting outwardly to provide projecting barbs.

In another embodiment of the invention, as depicted in FIGS. 3–4A, stent 10 has substantially the same overall configuration as that shown in FIG. 1 with the exception of the location of notched connecting members 20. As can be seen in FIG. 3, stent 10 is in a flattened condition and first stent section 11 is offset from second stent section 12, and each section is joined to the other by notched connecting members 20. Unlike the stent of FIG. 1, which required radial expansion to deform notched connecting members 20, the stent of FIG. 3 must be twisted to deform notched connecting members 20.

As seen in FIGS. 4 and 4A, unexpanded stent 10 now has notched connecting members 20 in alignment with the longitudinal axis of the stent and first stent section 11 is axially aligned with second stent section 12. By moving first stent section 11 in axial alignment with second stent section 12, notched connecting members 20 will deform at notch 21 resulting in projecting barb 22. To insure that projecting barb 22 forms radially outwardly, during the twisting motion first stent section 11 and second stent section 12 must be constrained so that they do not lengthen and change the overall length of stent 10. As can be seen in FIG. 4B, stent 10 has been rolled into its cylindrical configuration with notched connecting members 20 angulated so that they are not axially aligned with the longitudinal axis of stent 10. Once first stent section 11 is rotated or twisted with respect to second stent section 12, it will bring notched connecting members 20 into axial alignment with the longitudinal axis of stent 10 and the weakened area of notch 21 will permit notched connecting members 20 to deform outwardly, thereby forming projecting barb 22.

Figure 5:
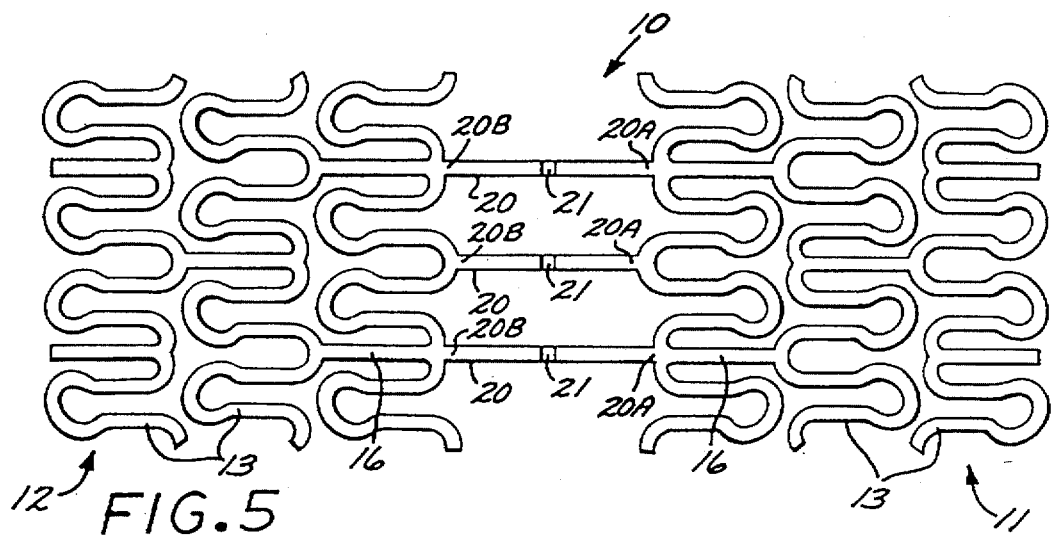
FIG. 5 is a plan view depicting another embodiment of the stent in which connector members having a notch separate two sections of the cylindrical elements.
Figure 5A:
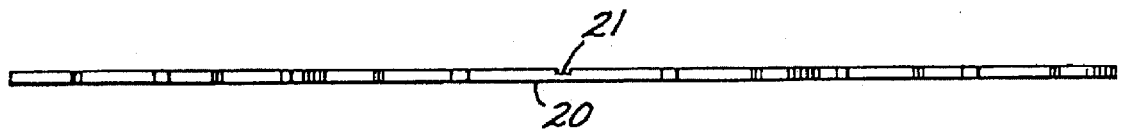
FIG. 5A is an elevational view of the stent of FIG. 5 in an unexpanded state and with the connector elements undeformed.
Figure 6:
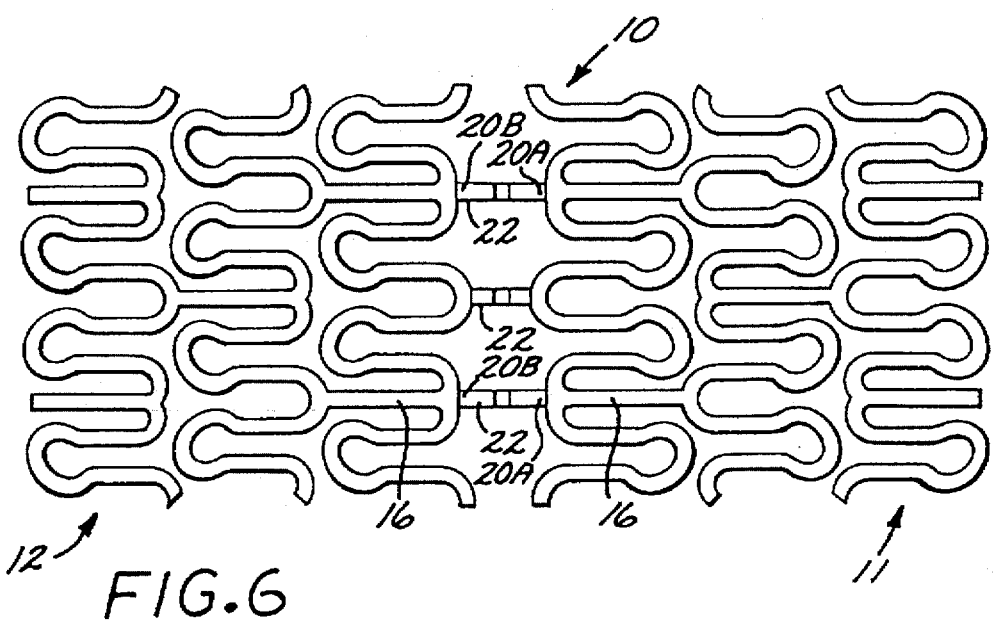
FIG. 6 is a plan view of the stent of FIG. 5 in which the two sections of cylindrical elements have been forced toward each other thereby deforming the connector members with a notch into providing projecting barbs.
Figure 6A:
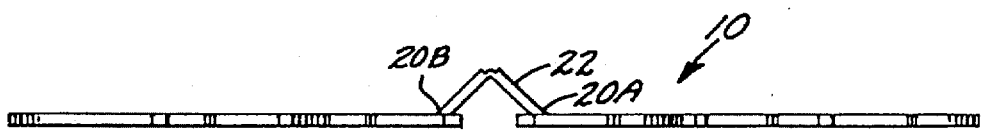
FIG. 6A is an elevational view of the stent of FIG. 6, in its unexpanded state, depicting the connector members having a notch deformed to provide projecting barbs.
Figure 6B:
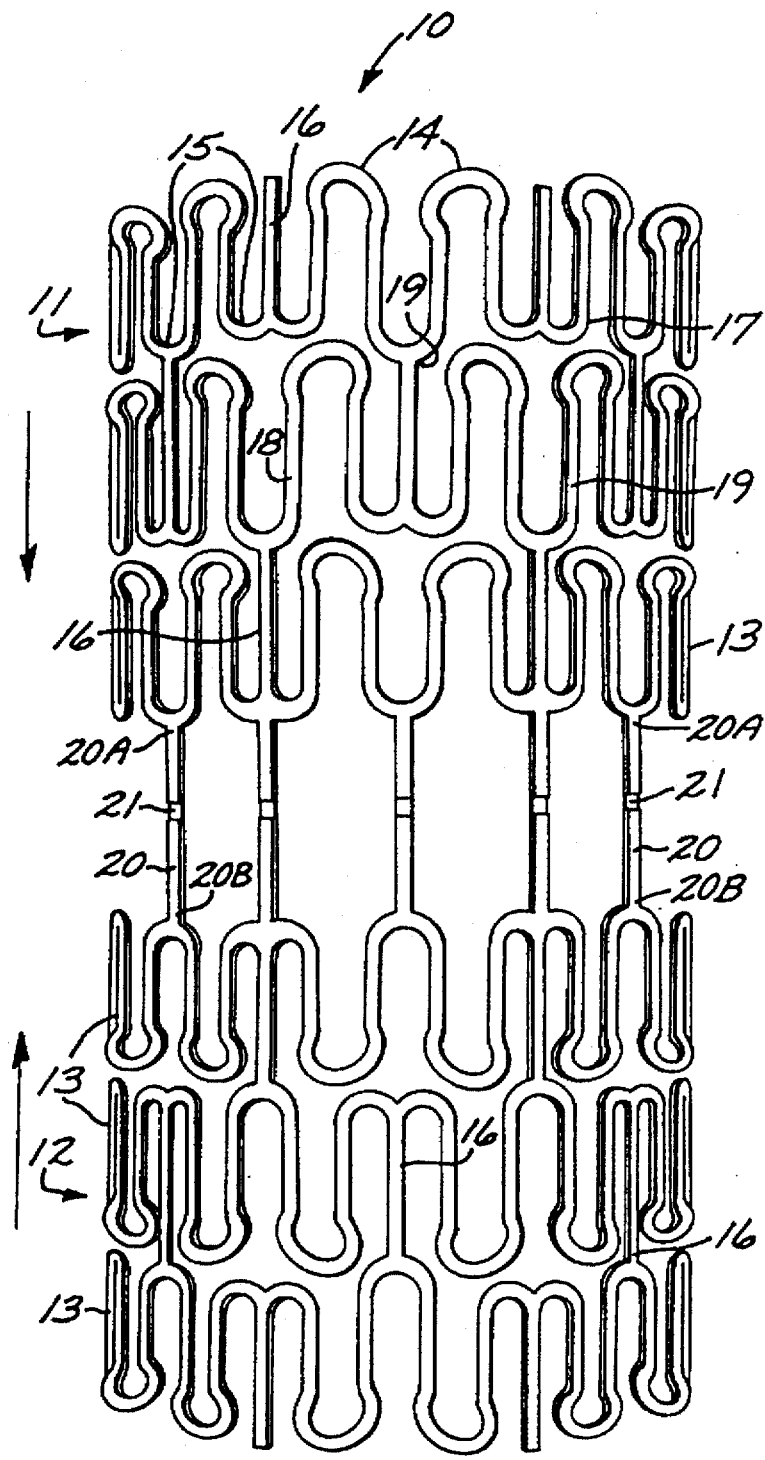
FIG. 6B is an elevational view of the stent of FIG. 6 in its rolled-up configuration before the stent ends are forced together to form projecting barbs.

In another embodiment of the invention as depicted in FIGS. 5–6B, stent 10 is comprised of a first stent section 11 and second stent section 12, each having a plurality of cylindrical elements 13. First stent section 11 is spaced apart from second stent section by notched connecting members 20 each having a notch 21 to form a weakened area. As with the other stent configurations, the cylindrical elements 13 are connected by connecting members 16. As can be seen more clearly in FIG. 6A, projecting barb 22 is formed when first stent section 11 and second stent section 12 are forced closer together, thereby causing notched connecting members 20 to deform outwardly and thereby form projecting barb 22. Thereafter, the stent can be expanded so that it expands from a first, low profile diameter to a second larger diameter to contact the vessel wall. As with all of the embodiments of the present invention, the first, unexpanded diameter of the stent provides a very low profile for delivery purposes through the patient's body lumen.

Figure 7:
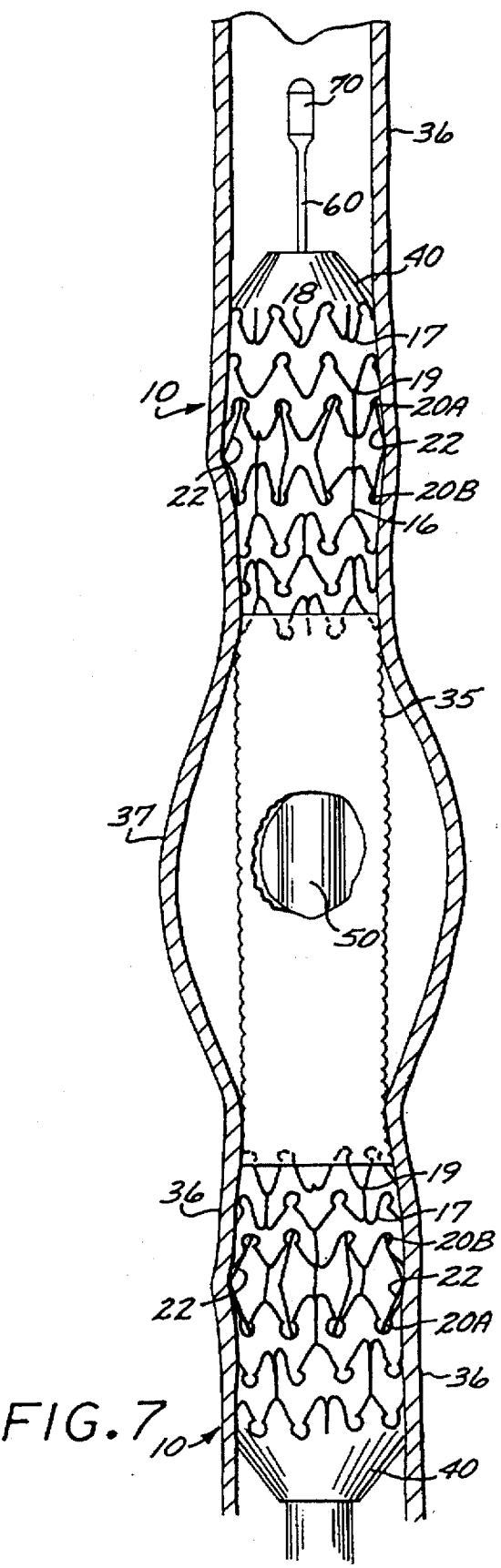
FIG. 7 is a partial cross-sectional view of a stent of the present invention attached to a tube graft and being implanted in a AAA procedure.

With respect to each of the embodiments shown in FIGS. 1–6C, each stent embodiment can be delivered intraluminally in much the same manner. Stent 10 can be mounted on the balloon portion of a delivery catheter and delivered intraluminally in a portion of a body lumen. Once stent 10 is positioned at the site where it is to be implanted, the balloon portion of the catheter is expanded by known means to expand the stent outwardly into contact with the body lumen. An example of one method of deploying stent 10 is depicted in FIG. 7. The balloon portion of a delivery catheter can be substituted for by any expansion member capable of receiving stent 10 and expanding or urging the stent outwardly into contact with a body lumen. Thus, other means are available to urge outwardly and expand stent 10 such as mechanical, hydraulic, pneumatic, and by phase transition using memory-shaped alloys or superelastic alloys.

As is shown in FIG. 7, stent 10 has been attached to an aortic tube graft 35 at both the distal end and proximal end of the tube graft. While a stent 10 is affixed to each end of tube graft 35, it is possible to attach a stent to only the distal end of tube graft 35, leaving the proximal end free. Due to the high pressure of blood flow in the aorta, the proximal end of tube graft 35 does not necessarily have to be firmly attached to the aortic wall 36. In FIG. 7, the stent and tube graft combination is mounted on balloon 40 and is delivered intraluminally by over-the-wire catheter 50. Generally, guidewire 60 having distal tip 70 is used to navigate the patient's vasculature and assist in positioning the catheter and balloon carrying the stent and tube graft combination. It is important to position the tube graft 35 so that it spans aneurysm 37 and completely diverts blood flow from the aorta through the tube graft, so that no blood flow leaks around the distal or proximal end of the tube graft and into aneurysm 37. Importantly, stent 10 should be expanded into the aortic wall 36 only where there is healthy tissue, and not where the aneurysm 37 has weakened the vessel wall.

Although a particular form of catheter has been described to route the graft-and-stent combination to the aneurysm, it will be apparent to those skilled in the art in treating aneurysms and similar conditions and of PTCA catheter design, that catheters having various configurations could be used successfully to perform the same functions. For example, well-known fixed wire and rapid exchange wire systems also can be used in the delivery system described above.

With further reference to FIG. 7, stent 10 of the present invention is shown in its expanded configuration with projecting barbs 22 projecting outwardly and penetrating aortic wall 36. With projecting barbs 22 penetrating aortic wall 36, stent 10 is firmly implanted and attached to aortic wall 36 so that there is no possibility of migrating once it is implanted. As shown in FIG. 7, the stent of FIG. 1C is used to anchor tube graft 35 to the aortic wall. Thus, balloons 40 are used to expand stent 10 radially outwardly thereby causing the notched connecting members 20 to deform and project outwardly forming projecting barbs 22. Importantly, the overall length of stent 10 does not appreciably change when it is expanded since connecting members 16A do not change in length and the first stent section 11 and second stent section 12 are constrained from moving toward each other during expansion.

The expansion properties of stainless steel make it a preferred material for stent 10. Other materials are contemplated, which include combinations of stainless steel and polymer materials. Further, other materials might be used including tungsten, platinum, gold or combinations of these materials in forming stent 10. Stent 10 can be formed from a flat sheet of material or from a single sheet of stainless steel tubing by chemically etching, laser cutting, or by using electronic discharge machining. A presently preferred mode of making stent 10 is found in co-pending application U.S. Ser. No. 08/345,501, entitled Method and Apparatus for Laser Cutting Small Objects, which is commonly assigned to Advanced Cardiovascular Systems, Inc. of Santa Clara, Calif. Other details of the various processes by which a stainless steel stent 10 can be manufactured can be found in co-pending U.S. Ser. Nos. 08/175,214 and 08/164,986, which are incorporated herein in their entirety by reference. Further details of chemically etching stent 10 can be found in U.S. Ser. No. 08/340,112, entitled Intraluminal Stent for Attaching a Graft, also commonly assigned to Advanced Cardiovascular Systems, Inc., Santa Clara, Calif.

It is also contemplated that the weakened portion of connecting member 20 result from something other than notch 21. In other words, it is intended that the invention not be limited to a weakened portion in the form of notch 21. Thus, the weakened portion of connecting member 20 can include an area along connecting member 20 that is thinner or hecked-down relative to the rest of the member. The weakened portion also can be formed by a metal different from the metal forming the rest of the stent or by selectively treating an area of the native material. For example, the first and second stent sections 11,12 can be formed from stainless steel, while a portion of connecting member 20 can be formed from any material having a lower modulus of elasticity which will deform and bend more easily than the stainless steel.

While the invention has been illustrated and described herein in terms of its use as an endoprosthesis for implanting in a body lumen such as a coronary artery or to be attached to a tubular graft or bifurcated graft for use in the aorta to repair an aortic aneurysm, it will be apparent to those skilled in the art that the stent can be used in other instances in other vessels of the body. Because the stent of the present invention has the novel feature of forming a positive attachment barb after the stent has been routed through a patient's vasculature to a specific site, and because it has a low profile during delivery, the stent is particularly well suited for implantation in almost any vessel where such devices can be used. These features, coupled with the fact that the stent does not retract or recoil to any great degree after it is radially expanded, provides a highly desirable support member for other types of endoprostheses.

Other modifications and improvements may be made without departing from the scope of the invention. For example, the various drawing figures depict several configurations of the stent and various sizes, each of which can be modified to suit a particular application without departing from the spirit and scope of the invention.

What is claimed is:

1. A method for implanting an intraluminal graft and stent assembly in a body lumen where said stent has a plurality of cylindrical elements which are expandable in a radial direction and which are interconnected so as to be aligned on a common longitudinal axis, and said stent having a plurality of connecting members for interconnecting said cylindrical elements, where at least some of said connecting members have a notch so that as said cylindrical elements are radially expanded said connecting members having a notch buckle outwardly to form a plurality of projecting barbs, said graft having a pair of ends and said stent being attached to said graft on at least one of said ends to form said graft and stent assembly, the method comprising:

provide a delivery catheter having an expandable member at a distal end;

mounting said graft and stent assembly on said expandable member of said catheter;

delivering said graft and stent assembly on said expandable member of said catheter percutaneously through the patient's vasculature to a specific location in a body lumen;

expanding said expandable member and thereby expanding said graft and stent assembly radially outwardly into contact with the body lumen;

forming a plurality of projecting barbs by deforming the connecting members having a notch so that they buckle outwardly such that each notch forms the apex of said projecting barbs, said projecting barbs penetrating the body lumen; and contracting said expandable member and withdrawing said catheter and said expandable member from the patient leaving said graft and stent assembly implanted in the body lumen.

2. The method of claim 1, wherein the delivering step further comprises positioning said graft and stent assembly across an abdominal aortic aneurysm so that said stent is positioned to expand into healthy tissue of the body lumen while at least a portion of said graft is positioned across the aneurysm.

3. The method of claim 1, wherein the graft is a tubular graft for positioning in a substantially straight segment of the body lumen.

4. The method of claim 1, wherein the graft is a bifurcated graft for positioning in a bifurcated section of the body lumen.

5. An expandable intraluminal graft and stent assembly for implanting in a body lumen, comprising:

a first stent section having a least one cylindrical element facing a first direction;

a second stent section having a least one cylindrical element facing a second direction opposite to said first direction;

a plurality of connecting members connecting said first section to said second section;

a weakened portion in a least some of said connecting members, said connecting members being deformable at said weakened portion to provide a plurality of projecting barbs, wherein the overall length of the stent in its unexpanded and expanded configuration is substantially the same; and a tubular graft having a first end and a second end, a first stent being attached to said first end and a second stent being attached to said second end to form said graft and stent assembly for implanting in the body lumen.

* * * * *